(12) United States Patent
Virtue et al.

(10) Patent No.: US 7,991,450 B2
(45) Date of Patent: Aug. 2, 2011

(54) METHODS AND SYSTEMS FOR VOLUME FUSION IN DIAGNOSTIC IMAGING

(75) Inventors: Patrick Michael Virtue, Waukesha, WI (US); Kathryn Mary Littlejohn, Wales, WI (US); Katherine Redford Phillips, Wauwatosa, WI (US); David Alan Littlejohn, Wales, WI (US); Diane M. Miesbauer, Hartland, WI (US); Andre Van Nuffel, Dilbeek (BE)

(73) Assignee: General Electric Company, Schenectady, NY (US)

( * ) Notice: Subject to any disclaimer, the term of this patent is extended or adjusted under 35 U.S.C. 154(b) by 573 days.

(21) Appl. No.: 11/824,833

(22) Filed: Jul. 2, 2007

(65) Prior Publication Data

US 2009/0012383 A1 Jan. 8, 2009

(51) Int. Cl.
*A61B 5/05* (2006.01)
*G06K 9/00* (2006.01)
(52) U.S. Cl. ........................................ 600/407; 382/128
(58) Field of Classification Search .................. 600/407; 382/128
See application file for complete search history.

(56) References Cited

U.S. PATENT DOCUMENTS

| | | | |
|---|---|---|---|
| 4,577,152 A | 3/1986 | Macovski | |
| 5,128,864 A | 7/1992 | Waggener et al. | |
| 5,307,264 A | 4/1994 | Waggener et al. | |
| 5,430,783 A | 7/1995 | Hu et al. | |
| 5,647,018 A | 7/1997 | Benjamin | |
| 5,673,300 A | 9/1997 | Reckwerdt et al. | |
| 5,694,530 A | 12/1997 | Goto | |
| 5,720,291 A | 2/1998 | Schwartz | |
| 5,740,222 A | 4/1998 | Fujita et al. | |
| 5,900,878 A | 5/1999 | Goto et al. | |
| 5,920,660 A | 7/1999 | Goto | |
| 6,947,584 B1 | 9/2005 | Avila et al. | |
| 6,990,231 B2 | 1/2006 | Goto | |
| 7,467,007 B2 * | 12/2008 | Lothert | 600/428 |
| 7,507,968 B2 * | 3/2009 | Wollenweber et al. | 250/363.07 |
| 2004/0122309 A1 | 6/2004 | Deller et al. | |

FOREIGN PATENT DOCUMENTS

| | | |
|---|---|---|
| JP | 08267292 A | 10/1996 |
| JP | 09156689 A | 6/1997 |

OTHER PUBLICATIONS

Nicholas Ayache (Ed.); Visualization of Multimodal Images for Neurosurgical Planning and Guidance, Lecture Notes in Computer Science, "Computer Vision, Virtual Reality and Robotics in Medicine", First International Conference, CVRMed '95, Nice, France, Apr. 1995 Proceedings; 10 pages.

(Continued)

*Primary Examiner* — Michael T Rozanski
(74) *Attorney, Agent, or Firm* — Dean Small; The Small Patent Law Group (57) ABSTRACT

Methods and systems for automatically fusing images are provided. The method includes acquiring scan data from a first imaging modality and fusing scan data from a second modality with the scan data from the first modality as scan data from the second modality is acquired and the method further includes displaying reconstructed images of the fused data.

23 Claims, 7 Drawing Sheets

OTHER PUBLICATIONS

Frederik Maes et al; Lecture Notes in Computer Science, "Computer-Aided Interactive Object Delineation Using an Intelligent Paintbrush Technique"; First International Conference, CVRMed '95, Nice, France, Apr. 1995 Proceedings pp. 77-83.

Jed Lengyel et al.; Lecture Notes in Computer Science, "Three-Dimensional Reconstructions and volume Rendering of Intravascular Ultrasound slices Imaged on a Curved Arterial Path"; First International Conference, CVRMed '95, Nice, France, Apr. 1995 Proceedings pp. 399-405.

Robert A. Drebin et al.; "Volume Rendering"; Computer Graphics, vol. 22, No. 4, Aug. 1988; pp. 65-74.

Karel J Zuiderveld et al.; "Multi-Modal Volume Visualization Using Object-Oriented Methods"; 0-8186-7067-3/95, 1995 IEEE pp. 59-66 and 129.

Max A Viergever; "Integrated Presentation of Multimodal Brain Images", Brain Topography, vol. 5, No. 2, 1992; pp. 135-145.

Markus Hardwiger et al.; "High-Quality Two-Level Volume Rendering of Segmented Data Sets on Consumer Graphics Hardware"; 8 pgs.

Jean-Jose Jacq et al; "A Direct Multi-Volume Rendering Method. Application to Visual Assessment of 3-D Image Registration Algorithms"; 10 pgs.

Paul J Keller, Phd, et al.; "MR Angiography with Two-dimensional Acquisition and Three-Dimensional Display"; Radiology, Nov. 1989, pp. 527-532.

Philippe G. Lacroute; "Fast Volume Rendering Using a Shear-Warp Factorization of the Viewing Transformation"; Technical Report: CSL-TR-95-678; Stanford Center for Integrated Systems, ARPA/ONR Contracts N00039-91-C-0138, 175-6212-1, NSF Contract CCR-9157767; 236 pages.

Pascal Volino et al.; Efficient Self-collision Detection on Smoothly Discretized Surface Animations using Geometrical Shape Regularity; MIRALab Copyright © Information 1998; MIRALab, University of Geneva; 18 pages.

* cited by examiner

METHODS AND SYSTEMS FOR VOLUME FUSION IN DIAGNOSTIC IMAGING

BACKGROUND OF THE INVENTION

This invention relates generally to imaging systems, and more particularly, to methods and systems for processing fused images in a Positron Emission Tomography/Computed Tomography (PET/CT) scanner workflow.

Time is typically a critical aspect of a PET/CT scan. For example, any delay caused during a post-processing workflow to verify that a hybrid registration is unacceptable and requires corrective action may be found after a tracer or contrast has left the area of interest or after a landmark is released. A scanner operator (e.g., for PET, CT, PET/CT, or any other type of modality) may spend considerable time manually finding and retrieving scanned images from a database into a fusion application. For instance, the operator may initially load image frames of CT scan data followed by PET scan data into a fusion viewer, or alternatively, the operator may load images of PET scan data followed by CT scan data into the fusion viewer. The operator may lose time monitoring the data transfer to an application workstation, lose time finding and launching the correct fusion application, as well as lose time in configuring batch processing and exporting parameters to save fused images. For instance, the operator may lose time verifying that the registration of the PET scan data with the CT scan data was correctly performed, which provides the functional data on top of a patient's physical anatomy. As an operator repeatedly executes these operations, mistakes may be made that may lead to additional delays. The delays may lead to significant time spent in a registration-correction application and may even require that the exam be performed again.

What is needed are systems and methods that automate a workflow by loading a CT dataset into a fusion viewer, dynamically loading a stream of PET images as the PET images arrive, and then displaying the fused PET/CT reformatted images in real-time, while minimizing the amount of time required to obtain such information. Thus, images would not have to be stored in memory and then made available to the viewer application, resulting in less than real-time viewing.

BRIEF DESCRIPTION OF THE INVENTION

In one embodiment a method for automatically fusing images is provided. The method includes acquiring scan data from a first imaging modality and fusing scan data from a second modality with the scan data from the first modality as scan data from the second modality is acquired. The method further includes displaying reconstructed images of the fused data.

In another embodiment, a diagnostic medical imaging system is provided. The diagnostic medical imaging system includes a scanner, a processor, and a display. The scanner acquires frames of image data from at least two imaging modalities. The processor is configured to load the scan data into a fusion viewer and utilize a fusion application to fuse the scan data from a second modality to the scan data from the first modality, as scan data from the second modality is acquired. The display outputs three-dimensional views of reconstructed images as the scan data from the second modality is acquired.

In yet another embodiment, a computer program embodied on a computer readable medium for controlling a diagnostic medical imaging system, which includes (i) a scanner to acquire frames of image data from a patient and (ii) a processor, is provided. The program includes a code segment that instructs the diagnostic medical imaging system to acquire image data from an object using at least two imaging modalities, load a complete image dataset from the first imaging modality into a fusion viewer, fuse image data from the second imaging modality, as the data is acquired, to the first imaging dataset, and display three-dimensional views of reconstructed images in real-time.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF THE INVENTION

In the following detailed description, reference is made to the accompanying drawings, which form a part hereof, and in which is shown by way of illustration specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

In this document, the terms "a" or "an" are used, to include one or more than one. In this document, the term "or" is used to refer to a nonexclusive or, unless otherwise indicated. In addition, as used herein, the phrase "pixel" also includes embodiments of the present invention where the data is represented by a "voxel." Thus, both the terms "pixel" and "voxel" may be used interchangeably throughout this document.

Also as used herein, the phrase "reconstructing an image" is not intended to exclude embodiments of the present invention in which data representing an image is generated, but a viewable image is not. Therefore, as used herein, the term "image" broadly refers to both viewable images and data representing a viewable image. However, many embodiments generate (or are configured to generate) at least one viewable image.

The systems and methods are generally directed toward multi-modal medical diagnostic imaging systems capable of scanning a patient using different modalities, such as, for example, but not limited to, Positron Emission Tomography (PET) and Computed Tomography (CT). The term "multi-modal" refers to systems that perform scans in different modalities, for example, CT and PET. It is contemplated that the benefits of systems and methods for analyzing an abnormality of an object accrue to different imaging systems, such as, for example, but not limited to, imaging systems including magnetic resonance imaging (MRI), single photon emission computed tomography (SPECT) imaging, and ultrasound imaging, among others.

In the various embodiments, different imaging modalities may be used. For example, in computed tomography (CT) imaging system configurations, an X-ray source projects a fan-shaped beam that is collimated to lie within an X-Y plane of a Cartesian coordinate system and generally is referred to as an "imaging plane." The X-ray beam passes through an object being imaged, such as a patient. The beam, after being attenuated by the object, impinges upon an array of radiation detectors. The intensity of the attenuated radiation beam received at the detector array is dependent upon the attenuation of an X-ray beam by the object. Each detector element of the array produces a separate electrical signal that is a measurement of the beam intensity at the detector location. The intensity measurements from all of the detectors are acquired separately to produce a transmission profile.

In third generation CT systems, the X-ray source and the detector array are rotated with a gantry within the imaging plane and around the object to be imaged such that the angle at which the X-ray beam intersects the object constantly changes. A group of X-ray attenuation measurements (e.g., projection data) from the detector array at one gantry angle is referred to as a "view." A "scan" of the object comprises a set of views made at different gantry angles, or view angles, during one revolution of the X-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units," which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed. Alternatively, an "axial" scan (e.g., a single rotation without the table moving) may be performed. Optionally, a "cine" scan (e.g., as the gantry spins during multiple cycles at the same location as multiple images are acquired during each turn of the gantry) may be performed.

Reconstruction algorithms for helical scanning typically use helical weighing algorithms that weight the collected data as a function of view angle and detector channel index. Specifically, prior to a filtered back projection process, the data is weighted according to a helical weighing factor, which is a function of both the gantry angle and detector angle. The weighted data is then processed to generate CT numbers and to construct an image that corresponds to a two dimensional slice taken through the object.

To further reduce the total acquisition time, multi-slice CT may be used. In multi-slice CT, multiple rows of projection data are acquired simultaneously at any instant of time. When combined with helical scan mode, the system generates a single helix of cone beam projection data. Similar to the single slice helical weighting scheme, a method can be derived to multiply the weight with the projection data prior to the filtered back projection algorithm.

At least some CT systems are configured to also perform PET imaging and are referred to as PET/CT systems. PET scanners incorporate a process similar to that found in CT, in that a map of the object attenuation can be generated. A method to perform this attenuation measurement includes the use of rotation rod sources containing positron-emitting radionuclides. The rods rotate outside the patient bore, but inside the diameter of the PET detector ring. Annihilation events occurring in the rods can send one photon into a near-side detector while a pair of photons traverses the object of interest in a manner similar to the CT X-ray. The data acquired from this method contains essentially the same image information as that acquired from the CT method except for the statistical quality of the resultant data. In the rotating rod case, the statistical quality is orders of magnitude inferior to most common CT scans. For the purpose of PET, data acquired in this manner is used to correct for the attenuation seen in the object by 511 keV photons from the annihilation events, which is often the most substantial correction performed on the PET data.

Positrons are positively charged electrons (anti-electrons) that are emitted by radio nuclides that have been prepared using a cyclotron or another device. The radionuclides most often employed in diagnostic imaging are fluorine-18 ($^{18}$F), carbon-11 ($^{11}$C), nitrogen-13 ($^{13}$N), and oxygen-15 ($^{15}$O), among others. Radionuclides are employed as radioactive tracers called "radiopharmaceuticals" that are incorporated into substances such as glucose or carbon dioxide.

To use a radiopharmaceutical in imaging, the radiopharmaceutical is injected into a patient and accumulates in an organ, vessel or the like, that is to be imaged. It is known that specific radiopharmaceuticals become concentrated within certain organs or, in the case of a vessel, that specific radiopharmaceuticals will not be absorbed by a vessel wall. The process of concentrating often involves processes such as glucose metabolism, fatty acid metabolism, and protein synthesis. Hereinafter, in the interest of simplifying this explanation, the organ to be imaged, including a vessel, will be referred to generally as an "organ of interest" or a "region of interest" and various embodiments of the invention will be described with respect to a hypothetical organ or region of interest.

After the radiopharmaceutical becomes concentrated within an organ of interest and while the radionuclides decay, the radionuclides emit positrons. The positrons travel a very short distance before they encounter an electron, and when the positron encounters an electron, the positron is annihilated and converted into two photons or gamma rays. This annihilation event is characterized by two features that are pertinent to medical imaging and particularly to medical imaging using PET. First, upon annihilation, each gamma ray has an energy of approximately 511 keV. Second, the two gamma rays are directed in nearly opposite directions (e.g., 180 degrees apart).

In PET imaging, if the general locations of annihilations can be identified in three dimensions, a three dimensional image of radiopharmaceutical concentration in an organ of interest can be reconstructed for observation. To detect annihilation locations, a PET camera is employed. An exemplary PET camera includes a plurality of detectors and a processor which, among other things, includes coincidence detection circuitry.

The coincidence circuitry identifies essentially simultaneous pulse pairs, which correspond to detectors that are essentially on opposite sides of the imaging area. Thus, a simultaneous pulse pair (e.g., the two gamma rays that are 180 degrees apart) indicates that an annihilation has occurred on a straight line between an associated pair of detectors. Over an acquisition period of a few minutes, millions of annihilations are recorded, where each annihilation is associated with a unique detector pair. After an acquisition period, recorded annihilation data can be used by any of several different well known image reconstruction methods to reconstruct the three dimensional image of the organ of interest.

Figure 1:
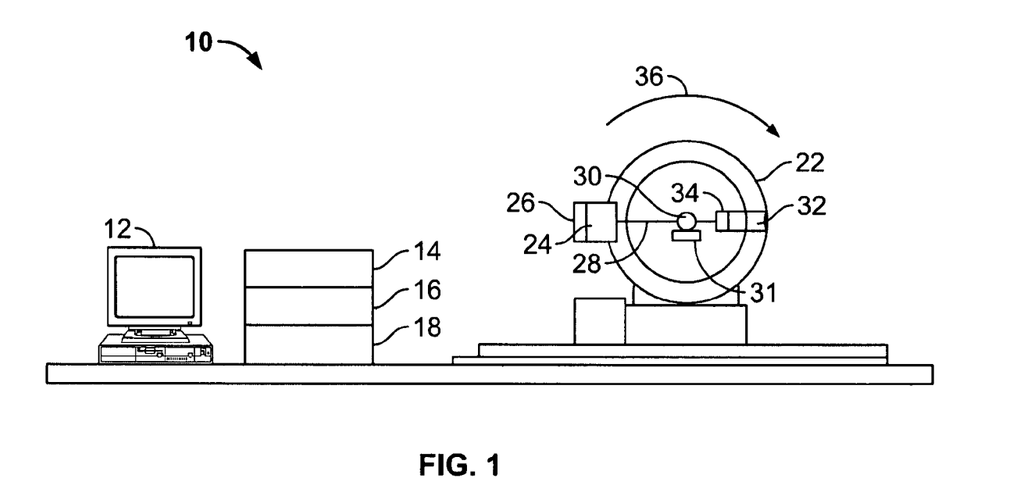
FIG. 1 is an illustration of an imaging system utilized in accordance with an embodiment of the present invention.

FIG. 1 is a schematic illustration of an embodiment of an imaging system 10. System 10 may include a controller work station, such as, a computer work station 12 that interfaces with a gantry motion controller 14, a patient bed motion controller 16, an x-ray tube high voltage supply, and a controller 18. A rotating gantry 22 has a first radial arm 24 that includes an x-ray emitting source 26 mounted thereon. The x-ray emitting source 26 is aligned such that the x-rays emitted by the x-ray emitting source 26 may be directed along an axis 28 toward an object 30. In the exemplary embodiment, object 30 may be a human patient, reclining supine upon a patient bed 31. Object 30 may include a radiopharmaceutical that concentrates in a predetermined region of the object 30 and emits emission gamma rays (described in connection with FIGS. 2 and 3 below). Gantry 22 includes a second radial arm 32 that includes one or more detector arrays 34 mounted thereon. As gantry 22 rotates in a direction 36, object 30 may be imaged with x-rays over a predetermined arc such that a plurality of image views are received, while object 30 remains positioned substantially directly between the x-ray emitting source 26 and the detector array 34 and in alignment with respect to axis 28. A field of view of imaging system 10 may be established by a width of detector array 34 in a plane of rotation. Detector array 34 may be translated in the plane of rotation to facilitate increasing an effective field of view of imaging system 10 during the rotation. Detector array 34 may be included in a plurality of imaging assembly modalities and/or multi-modality imaging assemblies, for example, any combination of a SPECT imaging assembly, a PET imaging assembly, a MRI imaging assembly, a CT imaging assembly, a Static X-Ray imaging assembly, a Dynamic (Fluoroscopy) X-Ray imaging assembly, and an ultrasound imaging assembly, among others.

A collimator (not shown) may be positioned in front of detector array 34 to prevent scattered radiation from contributing to the image. When an x-ray CT image is acquired, the x-ray emitting source 26 may be turned on, and data from detector array 34 may be output to the computer work station 12, which may process the data and generate a tomographic image. Data from the detector array 34 may include, for example, a pixel position, a gantry angle of rotation, and x-ray energy. Detector array 34 may include read-out electronics. Alternatively, x-ray emitting source 26 may be configured for continuous operation but may include a shutter (not shown) to facilitate blocking the x-rays from exiting the x-ray emitting source 26.

As another example, when acquiring a SPECT image, the x-ray emitting source 26 may be turned off or the shutter may be closed, and the object 30 may be injected with a radioactive tracer compound that migrates to regions of interest within the object 30. Gamma rays emitted by the radioactive tracer compound are received by the detector array 34, and the gamma ray pixel position, the gantry angle, and the gamma-ray energy data may be transmitted to the computer work station 12 for image generation. A collimator in front of the detector array 34 may facilitate ensuring that only gamma-rays that are emitted normal to the detector, or along another predetermined set of projection angles, contribute to the energy received.

An X-ray CT and a SPECT image may be sequentially acquired when the x-ray emitting source 26 is switched on, such that the x-rays from the x-ray emitting source 26 only reach the detector array 34 during a CT scan, and during a SPECT scan, the x-ray emitting source 26 may be switched off or a shutter may be moved in place to block substantially all the x-rays from the x-ray emitting source 26 from reaching the detector array 34. The detector array 34 in one embodiment is, for example, a cadmium zinc Telluride (CZT) detector array. The CT and SPECT image data may be processed by separate processors that may be configured to facilitate processing the particular energy level and the rate of receipt of photons from each modality.

Figure 2:
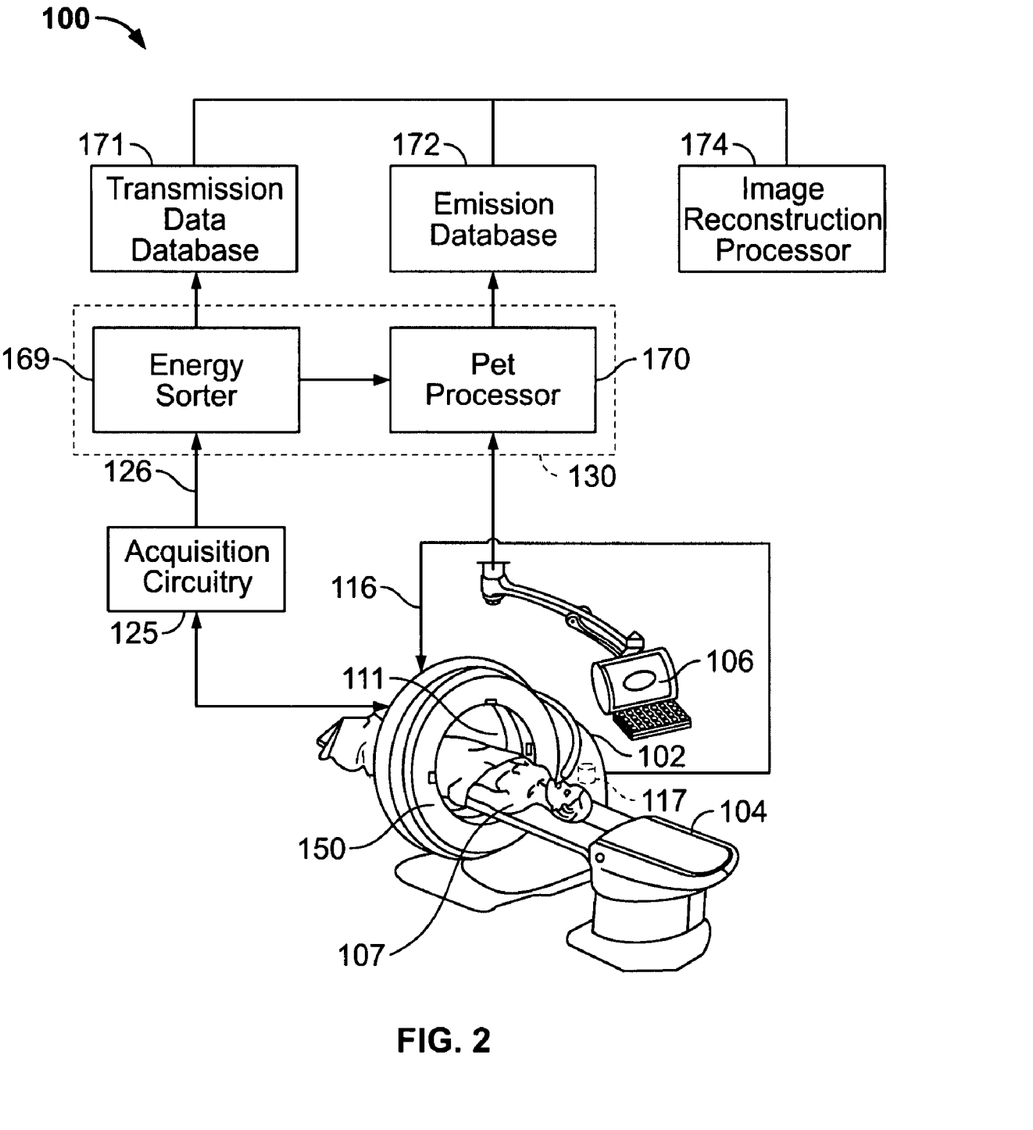
FIG. 2 is an illustration of a dual PET/CT imaging system formed in accordance with an embodiment of the present invention.

FIG. 2 is a block diagram of a medical imaging system 100 formed in accordance with another embodiment of the present invention. The system may be any emission-type computed tomography imaging system including, but not limited to a single PET scanner, a dual PET/CT scanner, a SPECT scanner, or a dual SPECT/CT scanner, among others.

The medical imaging system 100, such as, for example, a PET/CT system, includes a gantry 102, a patient table 104, and a computer system 106. Gantry 102 provides mechanical support for mounting devices such as, for example, detectors, scanners and transmitters (as described in FIG. 1 above) that are useful for scanning a patient 107. Gantry 102 houses imaging devices such as, for example, PET detectors. The PET system may be a stationary annular detector and, optionally, may include a pin source for PET.

The imaging devices on gantry 102 acquire image data by scanning a patient 107 lying on patient table 104. Moving the patient table 104 enables the scanning of various parts of the patient 107. Patient table 104 lies along the axis of gantry 102, which is known as a viewing area axis (as shown in FIG. 2) and can be moved along this viewing area axis. The patient table 104 can be positioned at various axial positions along the viewed area axis. The gantry 102 includes a plurality of detectors that are fixed and spaced on the gantry 102. The detectors are positioned radially outward from the viewing area axis along the gantry 102. Alternatively, the gantry 102 includes a plurality of detectors that are rotatable about the viewing area axis. The positioning of the detectors enables the scanning of various parts of the patient at different axial positions. For CT imaging, for example, a rotating detector and a source, and optionally including, a stationary detector ring may be provided.

Computer system 106 controls, for example, the positioning of patient table 104. Specifically, the computer system 106 is programmed or may receive user inputs used to control the positioning of the patient table 104 at a plurality of axial positions along the viewing area axis. The positioning of the table 104 enables the scanning of different axial positions of the patient 107. The computer system 106 may further be programmed to keep track of the various positions of the patient table 104. The computer system 106 may also be programmed to receive image data collected during scanning. In accordance with various embodiments of the invention, the computer system 106 may include a processor, such as a Linux® based or a Windows® based operating system, for a user interface and may include custom array processor boards for image reconstruction.

A scan time may also be fixed or predetermined, for example, by a user or computer system 106. In the case where the user predetermines the scan time, computer system 106 may receive an indication of the scan time. This indication may be used by computer system 106 to control the scanning. In addition to providing the scan time, the user may also provide to the computer system 106 an indication of the location of a volume of interest. The volume of interest is that part of the patient which is to be scanned (e.g., an organ, a tissue, a specific region of interest, and the like). In one embodiment, the volume of interest may be selected by a user and input to computer system 106. In various embodiments of the invention, the computer system 106 controls medical imaging system 100 to acquire the transmission data and determine a volume of interest based on the scan data. In an embodiment of the invention, the computer system 106 controls medical imaging system 100 to perform, for example, at least one of a CT scan, a PET transmission scan, and a CT scout scan to acquire the transmission data. In various embodiments of the invention, the computer system 106 is programmed to automatically move a volume of interest from a first position corresponding to a frame that includes a first axial periphery of the volume of interest to a second position corresponding to a frame that includes a second axial periphery of the volume of interest. In an embodiment of the invention, the computer system 106 moves the volume of interest in response to a user input. In another embodiment of the invention, the computer system 106 automatically moves the volume of interest based on the transmission data.

In addition, the medical imaging system 100 may include a transmission source (not shown). The transmission source (e.g., x-ray source) is located such that the signals transmitted by the transmission source pass through the volume of interest of the patient 107. The signals may be attenuated when the signals pass through a volume of interest of the patient 107. Hence, the detectors may collect data that is attenuated as data is collected after the transmission signals pass through the patient 107. The transmission source is, thus, used to acquire attenuation data relative to the patient 107. In accordance with an embodiment of the invention, computer system 106 may be programmed to generate the attenuation data relative to the patient 107 using the transmission source. The computer system 106 may further be programmed to determine the scan time for a frame of image data based on the attenuation data. Each frame of image data is a part of image data that corresponds to an axial position of the patient 107. Moving the patient table 104 along the viewing area axis enables the scanning of different axial positions of the patient 107. In various embodiments of the invention, the computer system 106 is programmed to modulate the time spent at a particular location of the patient table 104. The modulation enables a user of the medical imaging system 100 to increase or decrease the acquisition time of a particular region of the body.

The attenuation data is received by the computer system 106. Computer system 106 may use the received attenuation data, for example, to determine the scan time for each frame of image data. Various processors, sorters, and databases may be used to acquire and manipulate the scan data, including, for example, emission and transmission data. The processors, sorters and databases of FIG. 2 include acquisition circuitry 125, an acquisition processor 130 (including a sorter 169 and a PET processor 170), a transmission data database 171, an emission database 172, and an image reconstruction processor 174. In various embodiments of the invention, acquisition processor 130 is programmed to acquire emission data in a list mode and sinogram mode, as described in more detail below, and generate the image based on the emission data acquired in the list mode, the emission data acquired in the sinogram mode and Time-of-Flight (TOF) information of the emission data. Other computing components may be included with the system, which have been omitted here in the interest of simplification.

In one embodiment, the sorter 169 provides the time, location, and energy data to the PET processor 170. The PET processor 170 generally uses the received data to identify pairs of data, also known as coincidence pairs, coincident pair lines and lines of response, corresponding to annihilation events that occurred inside the region of interest. After the acquisition processor 130 identifies an annihilation event, the acquisition processor 130 provides the data to a viewer application (e.g., fusion viewer) to fuse the PET image data with CT image data while the PET image data is still being acquired, as described in more detail below. The acquisition processor 130 then updates data in the emission database 172 to store information relating to the annihilation event.

The image reconstruction processor 174 may access the data (e.g., emission and/or transmission data) in databases 171 and 172 continuously or periodically. The image reconstruction processor 174 uses the accessed data to generate images that may be requested by a system operator or generated automatically as described below. The operator can use computer system 106 to select image types and views.

Figure 3:
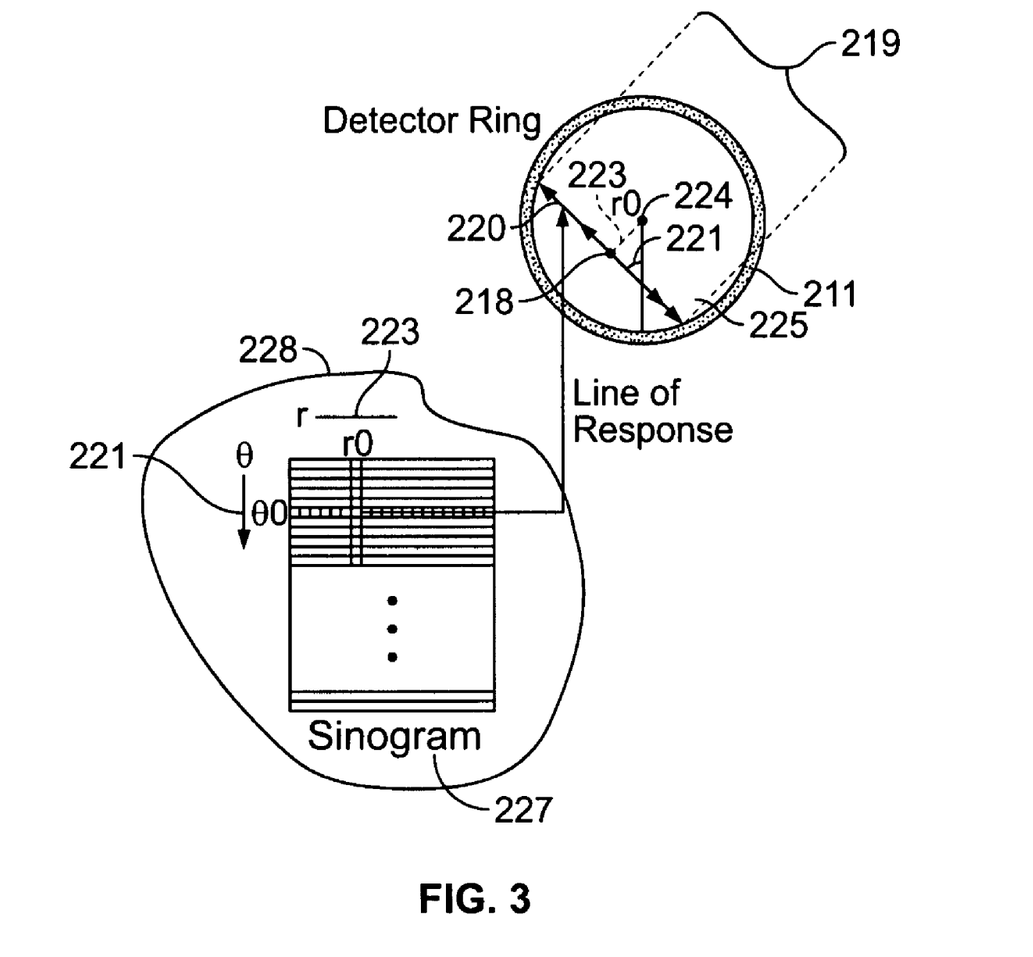
FIG. 3 is a diagram of a detector ring and an illustration of the construction of a sinogram formed in accordance with an embodiment of the present invention.

FIG. 3 is a diagram of a detector ring 211 and an illustration 228 of the construction of a sinogram 227 formed in accordance with an embodiment of the present invention. In positron emission tomography (PET), sorter 169 (shown in FIG. 2) receives a coincidence event pair 219 of an annihilation event 218 and identifies a corresponding line of response 220. Each line of response 220 may be identified by an angle (θ) 221 and a distance (r) 223 from a center 224 of the field of view 225. The array of the responses 220 is known as a sinogram 227.

System 100 has multiple rings 211 of detectors covering, for example, in one embodiment, 15-25 centimeters in the axial direction. Detectors typically include radiation detectors with sufficiently high timing resolution. The high timing resolution may be used to discriminate between at least two positions along the line of response 220 joining two such detectors. The photons are emitted in opposite direction along the line of response 220 and are simultaneously detected by detectors placed on the line of response 220.

PET data may be acquired in either a two-dimensional or a three-dimensional mode. In the two-dimensional acquisition mode, lines of responses 220 occurring in the same ring 211 or immediately adjacent ring 211 are accepted. In the three-dimensional mode, any line of response 220 occurring between any pair of detector rings 211 is acquired. In the two-dimensional mode, the coincident events 219 that are acquired within the same detector ring 211 contribute to the direct planes, while those events 219 across neighboring rings 211 contribute to the cross planes.

Although the specific embodiment mentioned above refers to a third generation CT system and a PET imaging system, the methods described herein equally apply to a fourth generation CT system (e.g., stationary detector and a rotating X-ray source), a fifth generation CT system (e.g., stationary detector and X-ray source), or other PET-only or nuclear systems wherein imaging is provided.

Figure 4:
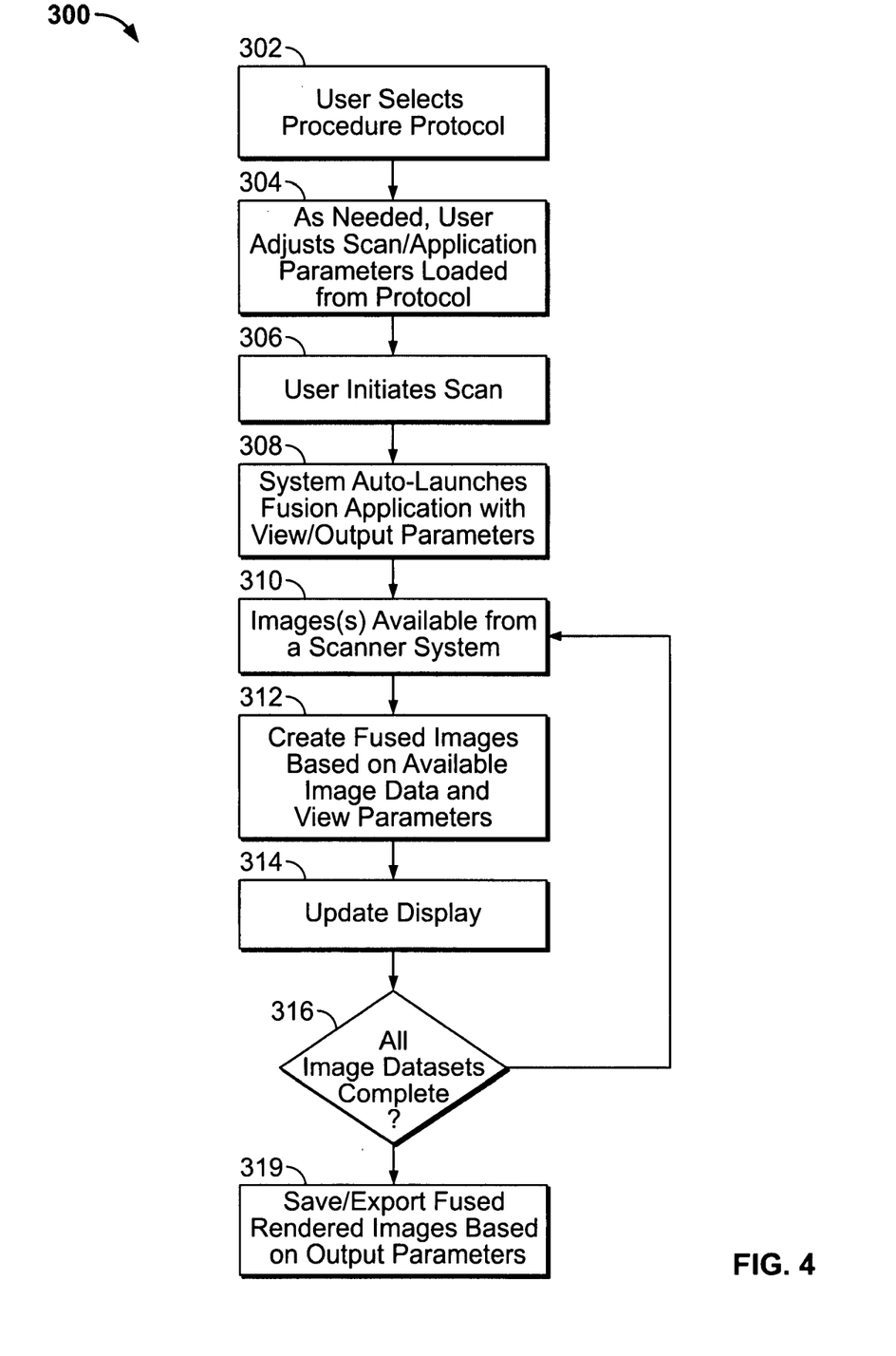
FIG. 4 is a flowchart illustrating a method for a PET/CT workflow utilized in accordance with an embodiment of the present invention.

FIG. 4 is a flow chart of a method 300 for performing a workflow using a dynamic fusion process in a multi-modality imaging system, for example, the system 10 (shown in FIG. 1), and the PET/CT imaging system 100 (shown in FIG. 2), in accordance with an embodiment of the present invention. At 302, a user selects a protocol, such as a scan prescription setting for each modality (e.g., CT scan, PET scan, SPECT scan, MRI scan, and the like). The scan protocol includes, for example, specifying scan parameters (e.g., a CT scan starting at 100 mm and ending at 700 mm with high quality and a PET scan starting at 100 mm and ending at 700 mm with 10 min per frame), auto-launching application settings (e.g., auto-launching a dynamic volume fusion application that automatically selects the fusion application and layout from a scan prescription), specifying the rendering parameters (e.g., the 3D view/render parameters), and specifying the application output parameters (e.g., output to a display, saving images locally to memory, exporting image files over a network, archiving image files, or sending images to be printed as a film). For instance, the 3D view/render parameters may be a list of settings that affect how the image may be rendered and the ultimate appearance of the rendered image. The parameters may include the orientation and location of the image to be rendered, the camera position and orientation in the case of 3D views, the dimensions of the volume visible within the image (e.g., height, width, and depth), and the selection of a rendering algorithm.

At 304, after the procedure protocol is loaded into the system, the user may adjust the scan parameters and/or application parameters that have been automatically loaded from the protocol, in order to customize a scan for a particular patient or procedure. For example, the user could adjust the start and end location of the scan and then change the dynamic volume fusion application settings to create coronal images instead of sagittal and send them to the PACS rather than film.

At 306, the user initiates a scan (e.g., a PET scan, a CT scan, a MRI scan, a SPECT scan, and the like) and scanning may begin. For example, the user may start two distinct scans, given a hybrid scanner.

At 308, the system 10 (shown in FIG. 1), and specifically the PET/CT imaging system 100 (shown in FIG. 2) then auto-launches a fusion application that includes view/output parameters and that fuses image data sets as described herein. The initial view of the application may be a set of blank viewports if no scanned image data is initially available.

At 310, the datasets are automatically loaded into the fusion application as the CT and PET images are available. The images may be loaded into the fusion viewer in any order. Thus, the system gradually generates a number of images for each scan over a period of time and notifies the application when each image or set of images is available. For example, the system produces one CT axial image every 0.25 second for 30 seconds and then produces one set of 50 PET axial images every 5 minutes. Alternatively, the user may select a set of available scan images from a scanner system, for example, from memory that may be loaded, for example, into a fusion viewer that reformats images or portions thereof for display as described herein. In an exemplary embodiment, the user may select to load a set of CT image data. Optionally, the user may select to initially load a set of PET image data. The data acquired may be at least one of image data, sinogram data, non-attenuated whole-body fluorodeoxyglucose (FDG) images, and the like. For instance, image data is a three-dimensional (3D) array of image data used as input to a rendering process. The values in the 3D array represent the intensities calculated by the scanner at a corresponding location in the patient's anatomy. Further, the 3D array may be constructed from a stack of 2D slices generated by the scanner.

At 312, as the application is notified of new image(s), the new image(s) are added to the correct volume in memory (e.g., CT images load into the CT volume, etc). Therefore, as the PET scan data is acquired, the PET scan data may be automatically fused based on the view parameters with the loaded CT scan data in the fusion viewer. The images are aligned based on registration information that defines the spatial relationship between the CT and PET datasets. For instance, the registration process may determine a common landmark or the origin of the same coordinate system that both the CT and PET datasets share. Fusion may be performed by blending two or more images together into a single rendered three-dimensional view. Fusion may include a blend of values from overlapping regions in at least two images. The real-time volume fusion integrates the fused images into the scanner workflow, and automatically fuses and renders the CT and PET images based on the application view/render settings. The fusion application may use at least two volumes of image data (e.g., a PET image dataset and a CT image dataset), which may be from different modalities or from the same modality (e.g., a MRI dataset). The fusion application also may use registration information in order to align the image volumes. Thus, as images are scanned, the images are fused and rendered in real-time for updating the display.

The rendering process converts the 3D volume data into a 2D rendered image based on the view/render parameters. The rendering algorithms may include a multi-planner reformat rendering (e.g., rendering axial, sagittal, coronal, or oblique cross-sections of the volume—which may include thin or thick slice cuts at a specific location and oriented through the object), a 3D maximum-intensity projection (MIP) rendering (e.g., 3D view of the volume where the output pixel values are determined by the greatest value along a specific viewing ray), or volume rendering (e.g., a 3D view of the volume where the output pixel values are determined by the accumulation of opacity and color values for data points along a specific viewing ray). The rendering process results in rendered image data that may be a 2D array of pixels representing the sampling and processing of the 3D image volume. The rendered image data may be displayed to a monitor screen or sent to another system for later display or printing.

Alternatively, a single modality may be utilized. For instance, when performing an MRI scan, (e.g., two images of the same anatomy having different contrasts or MRI images using different scan acquisition techniques to produce datasets with different contrast), a first image using a first contrast agent may be loaded in the fusion viewer, and as the second set of images are acquired using a second contrast agent, the two sets of images may be fused as the second set of images are acquired in real-time.

Optionally, multiple sets of images of different modalities may be loaded into the fusion viewer, and then another set of images may be fused in real-time as the images are acquired (e.g., images of yet another, but different, modality or images using a different contrast agent to enhance the image). For instance the rendering of the images may be fused rendered. Such real-time registration of images from different modalities allows an operator to determine early during the process whether, for example, the functional data is accurately being registered with the physical anatomy. Alternatively, once all of the CT and PET images are generated and loaded into the fusion auto-viewer, the process 300 may automatically fuse the images and save the fused images in memory.

Figure 5:
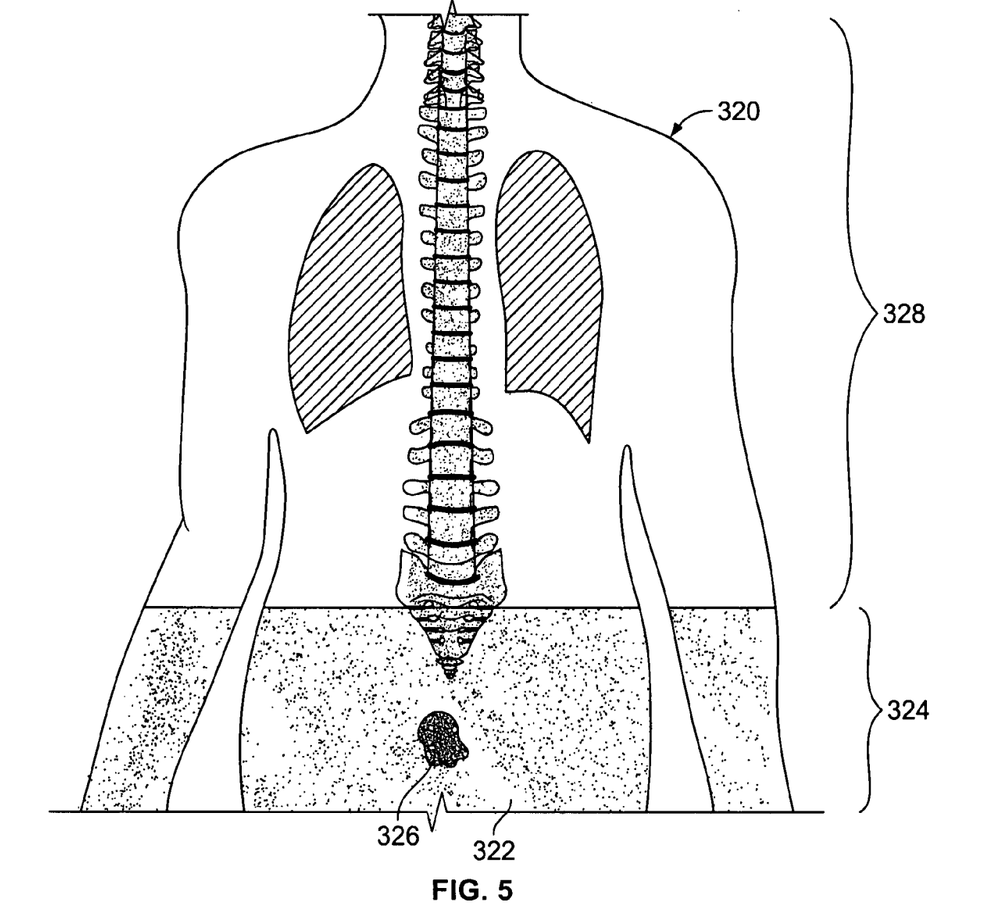
FIGS. 5, 6 and 7 illustrate exemplary examples of screen shots that display the dynamic loading of PET images in real time in accordance with an embodiment of the present invention.
Figure 6:
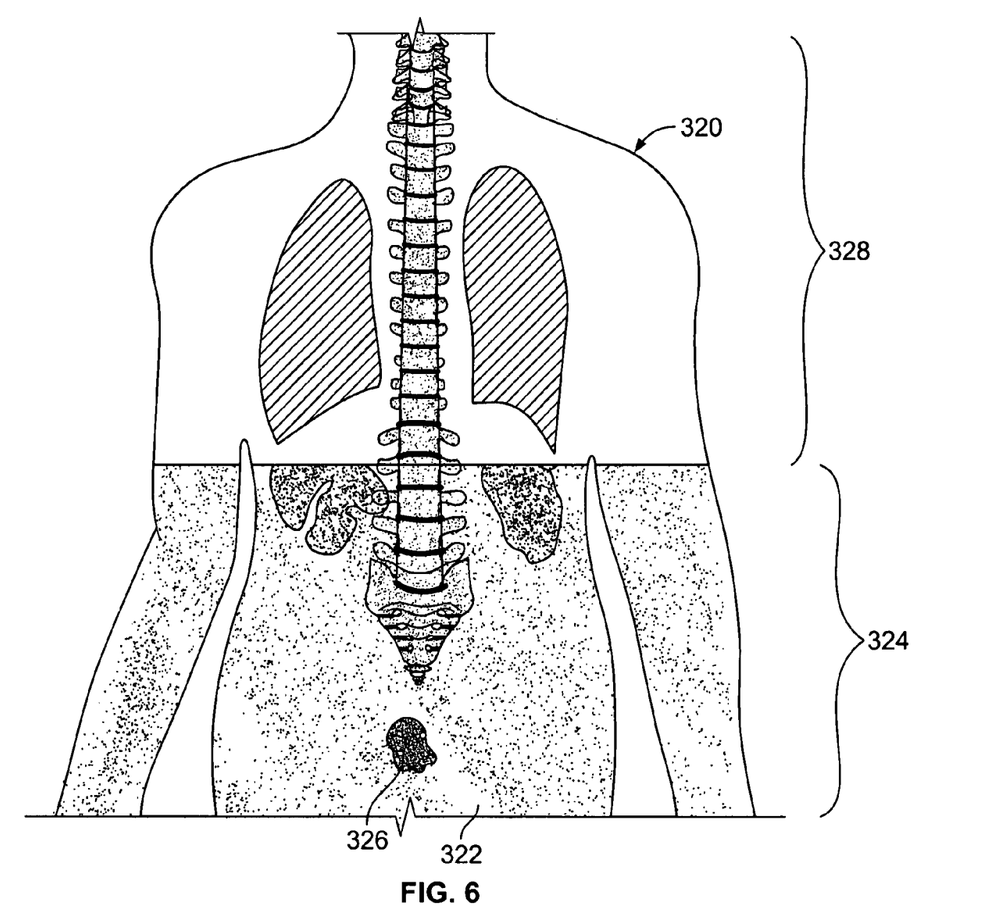
Figure 7:
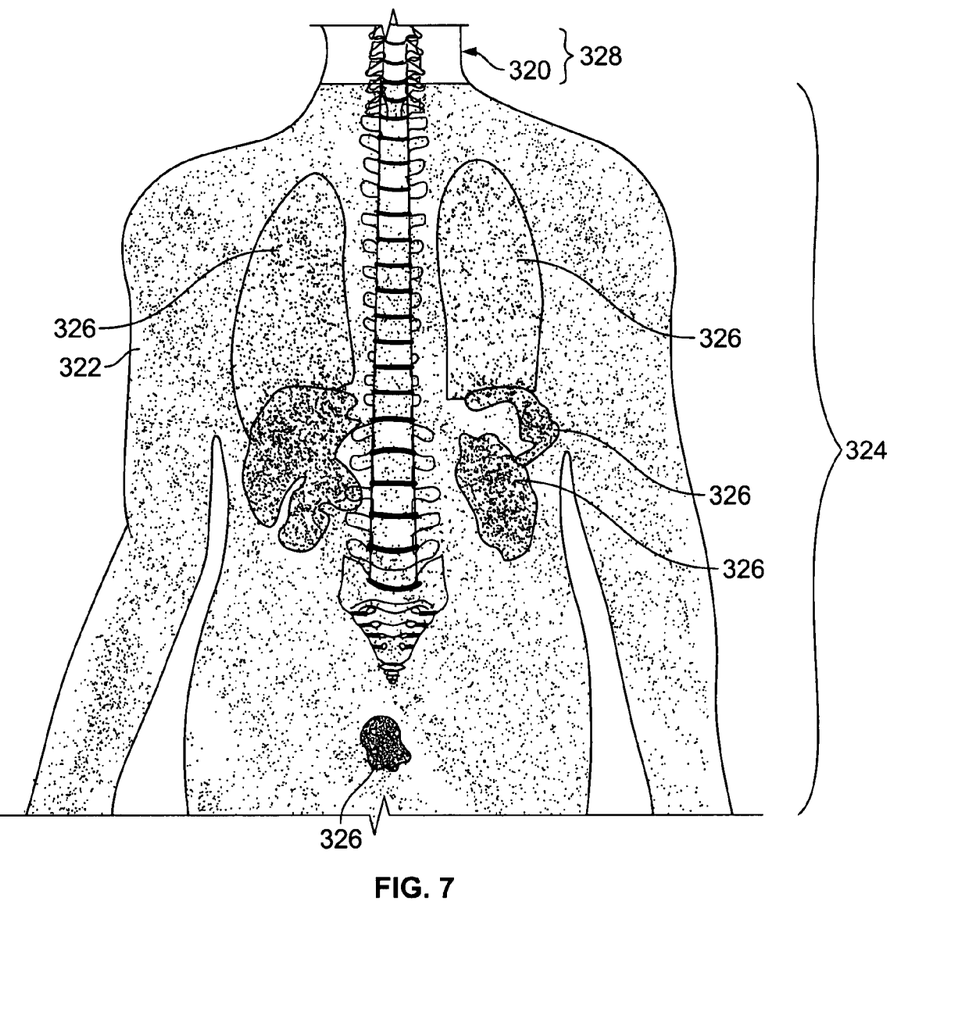

At 314, the display is updated or refreshed with fused views depicting regions of the patient data that have been processed by one or many scans. The 3D fusion views are updated in real-time, which allows the operator to verify the scan and the quality of each frame without having to wait until the PET scan is completed. Furthermore, the operator may check to see if any corrections are required. Therefore, the operator may review the images to visually verify, for example, whether the fusion is accurate, whether the scan range is acceptable, and whether the patient moved during the scan. In addition, the operator can determine if the registration of the CT image and PET image is correct or acceptable as the PET images are fused with the CT images. Thus, the operator may verify that the functional data overlays the physical anatomy correctly. Additionally, the operator also may check the hybrid scan quality and the overall quality of the image as the display is updated in real time. FIGS. 5, 6 and 7 are exemplary screen shots that display the dynamic loading of PET images in real time in accordance with an embodiment of the present invention. FIGS. 5, 6, and 7 illustrate the fusion of images from two modalities, specifically the fusion of a CT image 320 and a PET image 322. The CT image 320 is a complete CT image of a patient 107 (as shown in FIG. 2). The CT image 320 is presented in the background and shows the physical anatomy of patient 107. As a PET image 322 is acquired, the PET image is fused 324 to the CT image 320. The fused image 324 indicates regions that are "hot" or concentrated with radionuclide activity 326. As additional PET images 322 are acquired and fused, the region of the CT image 328 dynamically decreases as the fused image region 324 dynamically increases. The dynamically decreasing region is the CT image, which is being taken up by the fused CT/PET image region. For example, FIG. 5 shows the initial fusion of CT image 320 with a PET image 322 as a fused image 324. FIG. 6 shows the progression as additional PET images 322 are acquired, with the fused image 324 increasing or updating in real-time. FIG. 7 shows an almost completely fused image 324 with a very small area remaining that displays only a CT image 328. By providing the fusion of the PET image 322 with the CT image 320 in real-time, an operator may review each PET image frame one frame at a time as the PET image frame is fused. In addition, the operator may ascertain, for instance, as the fusion occurs whether the registration of the CT image 320 with the PET image 322 is accurate. In addition, dynamically providing fused images 324 allows the operator to make corrections as the PET scan progresses.

Returning to FIG. 4, at 316, the method 300 determines whether all the image datasets have been loaded into the fusion viewer. The fused images may be reviewed by outputting the fused images (e.g., CT images fused to a real-time PET image) to a display. As the PET image data is acquired, the PET image data is fused to the CT image data. The operator may review each fused image for each PET image frame one frame or section at a time as described above. In one embodiment, the scanned images are dynamically loaded for fusion. If additional scanned images need to be fused, the process flows back to step 310. However, if all the scanned images have been fused together, the process continues to step 319.

At 319, the completed fused three-dimensional images may be saved to memory. Alternatively, an auto batch processing application may be provided, where the fused image views are saved to memory, automatically networked to a remote computer, to a physician's workstation or personal digital assistant or cell phone, or automatically printed as a film. Alternatively, the fused images may be exported to other applications. For instance, a stack of fused coronal images may be processed and then networked to a PACS system. Optionally, the auto batch processing may be used with a variety of view layouts, including both fused views, as well as views of individual datasets. The user may select to repeat method 300 upon completion.

The various embodiments or components thereof may be implemented as part of a computer system. The computer system may include a computer, an input device, a display unit, and an interface, for example, for accessing the Internet. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device can also be other similar means for loading computer programs or other instructions into the computer system.

As used herein, the term "computer" may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer."

The computer or other processing machine executes a set of instructions (e.g., corresponding to the method steps described herein) that are stored in one or more storage elements (also referred to as computer usable medium). The storage element may be in the form of a database or a physical memory element present in the processing machine. The storage elements may also hold data or other information as desired or needed. The physical memory can be, for example, but not limited to, an electronic, magnetic, optical, electromagnetic, infrared, or semiconductor system, apparatus, device, or propagation medium. More specific examples of the physical memory include, but are not limited to, the following: a random access memory (RAM) a read-only memory (ROM), an erasable programmable read-only memory (EPROM or Flash memory), a Hard Disc Drive (HDD) and a compact disc read-only memory (CDROM).

The set of instructions may include various commands that instruct the processing machine to perform specific operations such as the processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

A technical effect of the various embodiments is to provide a method that automates a workflow in an diagnostic imaging system by loading the CT dataset into the fusion viewer, dynamically loading a stream of PET images as the images arrive, fusing the images, and then displaying the fused CT/PET reformats in real-time. Thus, saving the operator time in finding and loading various image datasets, and determining the correct fusion application, as well as minimizing the amount of time required by the operator to obtain such information. In various embodiments of the invention, the method of automating a workflow in a diagnostic imaging system can be implemented in software, hardware, or a combination thereof. The methods provided by various embodiments of the present invention, for example, can be implemented in software by using standard programming languages such as, for example, C, C++, Java, and the like.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus limiting as to the types of memory usable for storage of a computer program.

The analysis described above may be performed on several different data sets. Calculations may be performed on individual slices or rings or detectors, groups of slices, all slices, or a select line of responses, specific r and θ ranges, and the like. The analyzed data set may be modified to focus on the motion of specific organs or structures. The physiological structure may include a biological organ, for example, the stomach, heart, lung or liver; a biological structure, for example, the diaphragm, chest wall, rib cage, rib, spine, sternum or pelvis; or a foreign object fiducial marker, for example, a marker placed for the purpose of gating; a tumor, or a lesion or sore, for example, a bone compression fracture.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A method of automatically fusing images, said method comprising:
   acquiring scan data from a first imaging modality;
   fusing scan data from a second imaging modality with the scan data from the first modality as the scan data from the second modality is acquired; and
   displaying reconstructed images of the fused data including dynamically decreasing a region of the reconstructed images corresponding to the scan data from the first modality and dynamically increasing a region of the reconstructed images corresponding to the scan data from the second modality.

2. The method according to claim 1, wherein the scan data from at least one of the first modality or the second modality comprises at least one of a computer tomography (CT) dataset and a positron emission tomography (PET) dataset.

3. The method according to claim 1, wherein the first modality comprises at least one of a CT imaging modality, a MRI imaging modality, a SPECT imaging modality, a static X-Ray imaging modality, a dynamic (Fluoroscopy) X-Ray imaging modality, an ultrasound imaging modality, or a PET imaging modality.

4. The method according to claim 1, wherein the second modality comprises at least one of a CT imaging modality, a MRI imaging modality, a SPECT imaging modality, a static X-Ray imaging modality, a dynamic (Fluoroscopy) X-Ray imaging modality, an ultrasound imaging modality, or a PET imaging modality.

5. The method according to claim 1, wherein fusing the scan data from a second modality with the scan data from the first modality comprises aligning the scan data from the first imaging modality with the scan data from the second imaging modality.

6. The method according to claim 1, wherein fusing the scan data from a second modality with the scan data from the first modality comprises fusing scan data from at least two imaging modalities.

7. The method according to claim 1, wherein fusing the scan data from a second modality with the scan data from the first modality comprises dynamically loading scanned images from the second imaging modality to update a three-dimensional (3D) fusion view.

8. The method according to claim 7, wherein loading the images comprises acquiring images from the second imaging modality in a sequential order.

9. The method according to claim 7, wherein loading the images comprises loading at least one of a partial dataset of images or a complete dataset of images.

10. The method according to claim 1, wherein acquiring the scan data from at least one of the first modality or the second modality comprises acquiring at least one of sinogram data, and non-attenuated corrected PET data.

11. The method according to claim 1, wherein acquiring the scan data from at least one of the first modality or the second modality comprises selecting a scan protocol that includes a particular scan prescription and automatically launches a fusion application.

12. The method according to claim 1, wherein the scan data from the first modality comprises anatomical data and the scan data from the second modality comprises functional data, and further comprising incrementally updating the display of the reconstructed images by incrementally overlaying the functional data on the anatomical data while displaying the reconstructed image of the fused data.

13. The method according to claim 1, wherein the first modality comprises a computed tomography (CT) imaging modality and the second modality comprises a positron emission tomography (PET) imaging modality, and a PET scan being longer than a CT scan, and further comprising updating views in the reconstructed images of the fused data before the PET scan is complete such that an incomplete PET image is overlaid on a complete CT image.

14. A diagnostic medical imaging system, comprising:
   a scanner to acquire frames of scan data from at least two imaging modalities;
   a processor configured to:
   i) load the scan data from the imaging modalities into a fusion viewer; and
   ii) utilize a fusion application to fuse scan data from a second modality to scan data from a first modality, as the scan data from the second modality is acquired; and
   a display for outputting three-dimensional views of reconstructed images of the fused data as the scan data from the second modality is acquired, and wherein the display of the reconstructed images of the fused scan data includes dynamically decreasing a region of the reconstructed images corresponding to the scan data from the first modality and dynamically increasing a region of the reconstructed images corresponding to the scan data from the second modality.

15. The system according to claim 14, wherein the scan data from the at least two imaging modalities comprises at least one of sinogram data, list mode data, and non-attenuation corrected positron emission tomography (PET) data.

16. The system according to claim 14, wherein the imaging modalities comprise at least one of a CT imaging modality, a MRI imaging modality, a SPECT imaging modality, a static X-Ray imaging modality, a dynamic (Fluoroscopy) X-Ray imaging modality, an ultrasound imaging modality, or a PET imaging modality.

17. The system according to claim 14, wherein the scan data from the imaging modalities comprises data acquired using different contrast agents.

18. The system according to claim 14, wherein the processor is configured to align scan data from the first imaging modality with scan data from the second imaging modality.

19. The system according to claim 14, wherein loading the scan data from the at least two imaging modalities comprises loading images from at least the second imaging modality as the scan data from the second imaging modality is acquired.

20. The system according to claim 14, wherein fusing comprises dynamically loading scanned images from the second imaging modality to update a three-dimensional (3D) fusion view.

21. The system according to claim 14, wherein the scan data from the first modality comprises anatomical data and the scan data from the second modality comprises functional data, and wherein the processor is further configured to incrementally update the display of the reconstructed images by incrementally overlaying the functional data on the anatomical data while displaying the reconstructed images of the fused data.

22. The system according to claim 14, wherein the first modality comprises a computed tomography (CT) imaging modality and the second modality comprises a positron emission tomography (PET) imaging modality, and a PET scan being longer than a CT scan, and the processor is further configured to update views in the reconstructed images of the fused scan data before the PET scan is complete such that an incomplete PET image is overlaid on a complete CT image.

23. A non-transitory computer readable medium for use in a diagnostic medical imaging system having (i) a scanner to acquire frames of image data from a patient and (ii) a processor, the computer readable medium including instructions that instruct the diagnostic medical imaging system to:
  i) acquire image data from an object using at least two imaging modalities;
  ii) load a complete image dataset from a first imaging modality into a fusion viewer;
  iii) fuse image data from a second imaging modality, as the image data from the second imaging modality is acquired, to the dataset from the first imaging modality; and
  iv) display three-dimensional views of reconstructed images of the fused data in real-time, wherein the display of the three-dimensional views of reconstructed images includes dynamically decreasing a region of the reconstructed images corresponding to the image dataset from the first modality and dynamically increasing a region of the reconstructed images corresponding to the image data from the second modality.

* * * * *